(12) United States Patent
Wiemker et al.

(10) Patent No.: US 12,340,527 B2
(45) Date of Patent: Jun. 24, 2025

(54) INTER- AND EXTRAPOLATION OF CHEST IMAGE AND MECHANICAL VENTILATION SETTINGS INTO A TIME LAPSE SERIES FOR PROGRESSION MONITORING AND OUTCOME PREDICTION DURING LONG TERM MECHANICAL VENTILATION

(71) Applicant: KONINKLIJKE PHILIPS N.V., Eindhoven (NL)

(72) Inventors: Rafael Wiemker, Hamburg (DE); Joerg Sabczynski, Hamburg (DE); Thomas Koehler, Hamburg (DE); Cornelis Petrus Hendriks, Eindhoven (NL); Roberto Buizza, Eindhoven (NL); Jaap Roger Haartsen, Eindhoven (NL); Stefan Winter, Aachen (DE); Michael Polkey, London (GB); Rita Priori, Eindhoven (NL); Nataly Wieberneit, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 424 days.

(21) Appl. No.: 17/903,160

(22) Filed: Sep. 6, 2022

(65) Prior Publication Data
US 2023/0107737 A1    Apr. 6, 2023

Related U.S. Application Data

(60) Provisional application No. 63/252,201, filed on Oct. 5, 2021.

(51) Int. Cl.
*G06T 7/38* (2017.01)
*A61B 6/50* (2024.01)
(Continued)

(52) U.S. Cl.
CPC ............... *G06T 7/38* (2017.01); *A61B 6/50* (2013.01); *A61M 16/022* (2017.08); *G06T 5/92* (2024.01);
(Continued)

(58) Field of Classification Search
CPC ......... G06T 7/38; G06T 5/92; G06T 2200/24; G06T 2207/10016; G06T 2207/10116;
(Continued)

(56) References Cited

U.S. PATENT DOCUMENTS

| | | | |
|---|---|---|---|
| 10,076,621 B2 * | 9/2018 | Robinson | A61B 6/463 |
| 2009/0136099 A1 * | 5/2009 | Boyden | G06T 7/0012 |
| | | | 382/128 |
| 2011/0286652 A1 | 11/2011 | Kabus | |
| 2015/0005659 A1 * | 1/2015 | Masumoto | A61B 6/032 |
| | | | 600/538 |

(Continued)

OTHER PUBLICATIONS

Fu, Yabo, et al. "LungRegNet: an unsupervised deformable image registration method for 4D-CT lung." Medical physics 47.4 (2020): 1763-1774. (Year: 2020).*

(Continued)

*Primary Examiner* — Stephen R Koziol
*Assistant Examiner* — Michael Kim Maiden
(74) *Attorney, Agent, or Firm* — Daniel H. Brean (57) ABSTRACT

A mechanical ventilation device comprising at least one electronic controller is configured to receive images of lungs of a patient undergoing mechanical ventilation therapy with a mechanical ventilator, the images being acquired over time and having timestamps; process the images to generate timeline images at corresponding discrete time points; and display a timeline of the timeline images on a display device.

14 Claims, 4 Drawing Sheets

(51) Int. Cl.
  *A61M 16/00* (2006.01)
  *G06T 5/92* (2024.01)
(52) U.S. Cl.
  CPC .............................. *G06T 2200/24* (2013.01);
    *G06T 2207/10016* (2013.01); *G06T 2207/10116* (2013.01); *G06T 2207/20092* (2013.01); *G06T 2207/30061* (2013.01)
(58) Field of Classification Search
  CPC . G06T 2207/20092; G06T 2207/30061; A61B 6/50; A61B 16/022; A61M 16/022; G16H 30/40; G16H 30/42
  See application file for complete search history.

(56) References Cited

U.S. PATENT DOCUMENTS

| | | | |
|---|---|---|---|
| 2016/0217576 A1* | 7/2016 | Kabus | G06T 7/11 |
| 2017/0206643 A1* | 7/2017 | Weiss | G06F 3/0485 |
| 2018/0260955 A1* | 9/2018 | Matsutani | G06T 7/38 |
| 2021/0334970 A1* | 10/2021 | Liu | G06T 7/0016 |
| 2021/0345865 A1* | 11/2021 | Spillinger | A61B 1/000094 |
| 2021/0407648 A1* | 12/2021 | Ravishankar | G16H 50/20 |
| 2022/0338929 A1* | 10/2022 | Goyal | G16H 50/50 |
| 2022/0378321 A1* | 12/2022 | Rehouma | A61B 5/1135 |
| 2024/0371013 A1* | 11/2024 | Low | G06T 7/30 |

OTHER PUBLICATIONS

Zhao, Bowen, et al. "Tissue-volume preserving deformable image registration for 4DCT pulmonary images." Proceedings of the IEEE conference on computer vision and pattern recognition workshops. (Year: 2016).*

International Search Report for PCT/EP2022/077090 filed Sep. 29, 2022.

Dmytrowich, J. et al., "Mechanical ventilation guided by electrical impedance tomography in pediatric acute respiratory distress syndrome". Journal of Clinical Monitoring and Computing. Springer Netherlands, Dordrecht, vol. 32, No. 3 (2017), pp. 503-550.

Walsh, B.K. et al., "Electrical Impedance Tomography During Mechanical Ventilation". Respir Care, vol. 61, No. 10 (2016), pp. 1417-1424.

Karbing, D.S. et al., "Journal of Clinical Monitoring and Computing 2018-2019 end of year summary: respiration". Journal of Clinical Monitoring and Computing, Springer Netherlands, Dordrecht, vol. 34, No. (2020), pp. 197-205.

Cao, J. et al., "3D aided duet GANs for multi-view face image synthesis", IEEE Trans. on Information Forensics and Security, vol. 14, issue 8 (Aug. 2019).

Wang, C. et al., "Head Pose Estimation via Manifold Learning", 2017 DOI: 10.5772/65903.

Roweis, S.T., et al., "Nonlinear Dimensionality Reduction by Locally Linear Embedding", Science vol. 290, 2000; https://en. wikipedia.org/wiki/Nonlinear_dimensionality_reduction.

Duque, A.F. et al., "Extendable and invertible manifold learning with geometry regularized autoencoders", arXiv:2007.07142, 2020.

Koniaris, B. et al., "Real-time Rendering with Compressed Animated Light Fields, Disney Research". Graphics Interface 2017.

Wang, Y. et al., "DeepOrgnNet: On-the-Fly Reconstruction and Visualization of 3D/4D Lung Models from Single-View Projections by Deep Deformation Network", arXiv: 1907.09375v1, 2019.

* cited by examiner

INTER- AND EXTRAPOLATION OF CHEST IMAGE AND MECHANICAL VENTILATION SETTINGS INTO A TIME LAPSE SERIES FOR PROGRESSION MONITORING AND OUTCOME PREDICTION DURING LONG TERM MECHANICAL VENTILATION

CROSS-REFERENCE TO RELATED APPLICATIONS

This patent application claims the priority benefit under 35 U.S.C. § 119 (e) of U.S. Provisional Application No. 63/252,201, filed on Oct. 5, 2021, the contents of which are herein incorporated by reference.

The following relates generally to the respiratory therapy arts, mechanical ventilation arts, mechanical ventilation monitoring arts, and related arts.

BACKGROUND

Mechanical ventilation (MV) of a patient typically entails placement of an endotracheal tube (ETT) into a trachea of the patient, in a process known as tracheal intubation. The desired position of the tip of an ETT is approximately 5.0 cm (±2.0 cm) above a carina (i.e., a location where the trachea splits into the main right and left bronchus). Tracheal intubation is usually performed by an anesthesiologist or other qualified medical professional, and in a common sequence the head is bent backward to access the airway, and a laryngoscope is used to facilitate proper placement of the ETT between the vocal cords and into the trachea, without misplacement into an esophagus. Other approaches for connecting a patient to a mechanical ventilator include a tracheostomy procedure in which an incision is made to directly access the trachea.

Common situations where mechanical ventilation is required can include intensive care unit (ICU) cases and during major surgery. Such patients often have images (e.g., computed tomography (CT) images) obtained of the thorax before being sent to the ICU, in particular if the patient's condition is a lung-related disease (e.g., Covid-19), or trauma.

For patients under prolonged periods of MV, regular imaging is applied to monitor disease progression, and also, for example, tube location, possible ventilation induced injury, etc. Daily bed-side X-ray images are not untypical. The settings of the MV (e.g., positive-end expiratory pressure (PEEP) and volumes) can be adjusted over time.

However, such current approaches have drawbacks. For example, X-ray images from different time points can vary in a projection geometry between an X-ray source, a sensor, and a patient, in particular if taken under the practical restrictions of mobile bed-side imaging. X-ray images from different time points can vary in their gray values dynamics, since they are X-ray intensities composed of attenuations superimposed along the ray, and taken with automatic exposure control. X-ray images from different time points can vary in the phase of the respiratory cycle at the moment of recording. In a stack of X-ray images, or in side-wise 'hanging', it is not easy to appreciate subtle changes in the images, because of the global gaze transition. The changing MV-settings are typically recorded in written form (e.g., as dated list entries), and it is tedious to align the MV documentation mentally with the time points of the X-ray images. If a 'rigid' (e.g., multi-linear) spatial and dynamic registration is applied between the images, then a high degree of visual 'flicker' (residual) remains between the images, making comparison difficult. If on the other hand a completely 'elastic' spatial and dynamic registration is applied between the images, then the differences may be reduced or even visually vanish completely, rendering the comparison futile, since also real anatomical change is suppressed or eliminated by the nonrigid registration. For estimation of future progression, it is difficult to mentally recollect and align similar images and MV settings, and to consider also experiences from other clinical sites.

The following discloses certain improvements to overcome these problems and others.

SUMMARY

In one aspect, a mechanical ventilation device comprising at least one electronic controller is configured to receive images of lungs of a patient undergoing mechanical ventilation therapy with a mechanical ventilator, the images being acquired over time and having timestamps; process the images to generate timeline images at corresponding discrete time points; and display a timeline of the timeline images on a display device.

In another aspect, a mechanical ventilation method comprises, with at least one electronic controller, receiving images of lungs of a patient undergoing mechanical ventilation therapy with a mechanical ventilator, the images being acquired over time and having timestamps; processing the images to generate timeline images at corresponding discrete time points; and displaying a timeline of the timeline images on a display device.

One advantage resides in providing a timeline of images of a patient undergoing MV.

Another advantage resides in providing a timeline of images of a patient undergoing MV to visualize progression of a condition of the patient over time.

Another advantage resides in providing a timeline of images of a patient undergoing MV to provide patient information or MV information at different time points in the timeline.

Another advantage resides in providing a timeline of images of a patient undergoing MV to provide predictions as to a condition of the patient over time.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

As used herein, the singular form of "a", "an", and "the" include plural references unless the context clearly dictates otherwise. As used herein, statements that two or more parts or components are "coupled," "connected," or "engaged" shall mean that the parts are joined, operate, or co-act together either directly or indirectly, i.e., through one or more intermediate parts or components, so long as a link occurs. Directional phrases used herein, such as, for example and without limitation, top, bottom, left, right, upper, lower, front, back, and derivatives thereof, relate to the orientation of the elements shown in the drawings and are not limiting upon the scope of the claimed invention unless expressly recited therein. The word "comprising" or "including" does not exclude the presence of elements or steps other than those described herein and/or listed in a claim. In a device comprised of several means, several of these means may be embodied by one and the same item of hardware.

Figure 1:
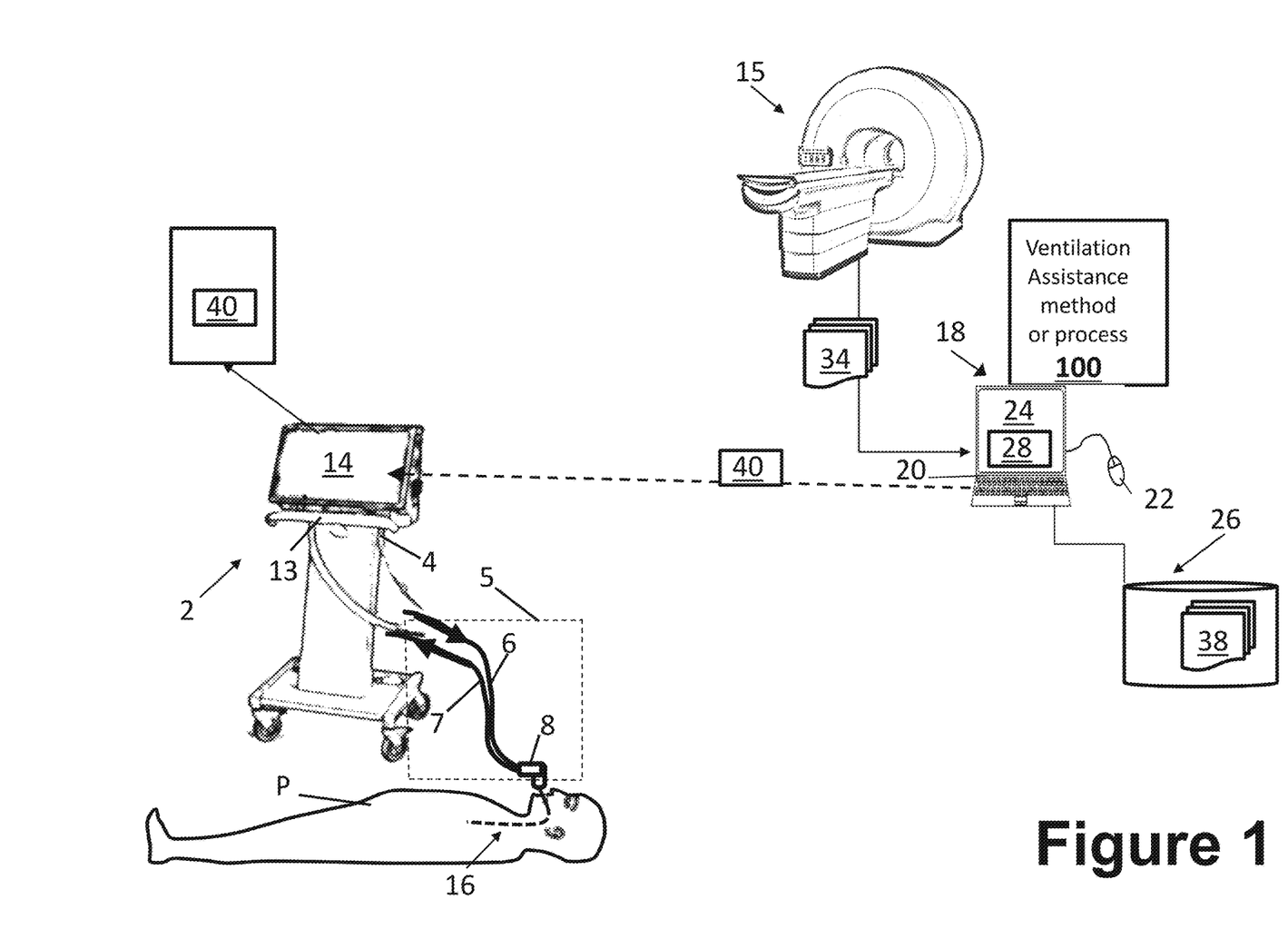
FIG. 1 diagrammatically shows an illustrative mechanical ventilation system in accordance with the present disclosure.

With reference to FIG. 1, a mechanical ventilator 2 for providing ventilation therapy to an associated patient P is shown. As shown in FIG. 1, the mechanical ventilator 2 includes an outlet 4 connectable with a patient breathing circuit 5 to delivery mechanical ventilation to the patient P. The patient breathing circuit 5 includes typical components for a mechanical ventilator, such as an inlet line 6, an optional outlet line 7 (this may be omitted if the ventilator employs a single-limb patient circuit), a connector or port 8 for connecting with an ETT, and one or more breathing sensors (not shown), such as a gas flow meter, a pressure sensor, end-tidal carbon dioxide ($etCO_2$) sensor, and/or so forth. The mechanical ventilator 2 is designed to deliver air, an air-oxygen mixture, or other breathable gas (supply not shown) to the outlet 4 at a programmed pressure and/or flow rate to ventilate the patient via an ETT. The mechanical ventilator 2 also includes an electronic controller (e.g., a microprocessor) 13 for controlling operation of the mechanical ventilator 2, and a display device 14 for displaying information about the patient P and/or settings of the mechanical ventilator 2 during mechanical ventilation of the patient P.

FIG. 1 also shows a medical imaging device 15 (also referred to as an image acquisition device, imaging device, and so forth). The image acquisition device 15 can be a Computed Tomography (CT) image acquisition device, a C-arm imager, or other X-ray imaging device; Magnetic Resonance (MR) image acquisition device; an ultrasound (US) image acquisition device; or a medical imaging device of another modality. As primarily described herein, the medical imaging device 15 comprises an X-ray medical imaging device 15. As described herein, the medical imaging device 15 is used to acquire images of the patient P, and is located in the same room as the patient P as shown in FIG. 1. It should be noted that the imaging device 15 may not be located in the same room, or even the same department, as the mechanical ventilator 2. For example, the medical imaging device 15 may be located in a radiology laboratory while the mechanical ventilator 2 may be located in an intensive care unit (ICU), cardiac care unit (CCU), in a hospital room assigned to the patient P, or so forth.

FIG. 1 diagrammatically illustrates the patient P intubated with an endotracheal tube (ETT) 16 (the lower portion of which is inside the patient P and hence is shown in phantom). Another patient interface may be used for the mechanical ventilation, such as a tracheostomy. The connector or port 8 connects with the ETT 16 or other patient interface to operatively connect the mechanical ventilator 2 to deliver breathable air to the patient P via the ETT 16. The mechanical ventilation provided by the mechanical ventilator 2 via the ETT 16 may be therapeutic for a wide range of conditions, such as various types of pulmonary conditions like emphysema or pneumonia, viral or bacterial infections impacting respiration such as a COVID-19 infection or severe influenza, cardiovascular conditions in which the patient P receives breathable gas enriched with oxygen, or so forth.

Figure 2:
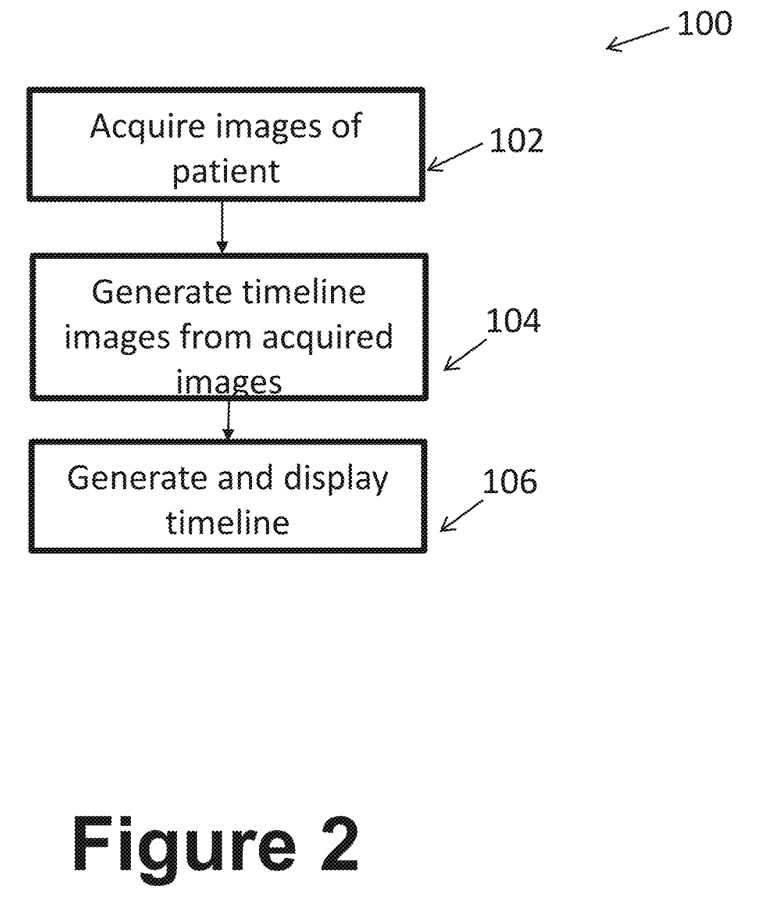
FIG. 2 shows an example flow chart of operations suitably performed by the system of FIG. 1.

With continuing reference to FIG. 1 and with further reference to FIG. 2, an electronic processing device 18 configured to assist with mechanical ventilation of the patient P. The electronic processing device 18 can comprise any suitable electronic processing device, such as a workstation computer (more generally, a computer), a smart device (e.g., a smartphone, a tablet, and so forth), or server computer or a plurality of server computers, (e.g., interconnected to form a server cluster, cloud computing resource, or so forth). The electronic processing device 18 includes typical components, such as an electronic controller 20 (e.g., an electronic processor or a microprocessor), at least one user input device (e.g., a mouse, a keyboard, a trackball, a finger swipe on a touchscreen of a smart device, and/or the like) 22, and at least one display device 24 (shown only in FIG. 1, e.g., an LCD display, plasma display, cathode ray tube display, and/or so forth). In some embodiments, the display device 24 can be a separate component from the electronic processing device 18. The display device 24 may also comprise two or more display devices.

The electronic controller 20 is operatively connected with a one or more non-transitory storage media 26. The non-transitory storage media 26 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage, an internal hard drive of the intubation assistance device 18, various combinations thereof, or so forth. It is to be understood that any reference to a non-transitory medium or media 26 herein is to be broadly construed as encompassing a single medium or multiple media of the same or different types. Likewise, the electronic controller 20 may be embodied as a single electronic processor or as two or more electronic processors. The non-transitory storage media 26 stores instructions executable by the at least one electronic controller 20. The instructions include instructions to generate a graphical user interface (GUI) 28 for display on the remote operator display device 24.

Furthermore, as disclosed herein, the non-transitory storage media 26 stores instructions executable by the at least one electronic controller 20 to perform ventilation assistance method or process 100. As described herein, the method 100 can be performed by the electronic processing device 18, or can be performed by the electronic controller 13 of the mechanical ventilator 2.

It will be appreciated that, as previously noted, the mechanical ventilator 2 can be disposed in the same room of the medical facility as the image acquisition device 15 and the electronic processing device 18. For example, the image acquisition device 15 can be a mobile X-ray imaging device, a mobile ultrasound imaging device, or so forth. Using a mobile imaging device is advantageous because the patient is not required to be transported to the image acquisition device 15, which is cumbersome when the patient is connected with the mechanical ventilator 2. In another example, however, the mechanical ventilator 2 and the electronic processing device 18 can be disposed in the first room, while the image acquisition device 15 is disposed in the second room of the medical facility. In a further example, each of the mechanical ventilator 2, the image acquisition device 15 and the electronic processing device 18 can be disposed in separate rooms of the medical facility. These are merely illustrative examples.

With reference to FIG. 2, and with continuing reference to FIG. 1, an illustrative embodiment of the intubation assistance method 100 is diagrammatically shown as a flowchart. At an operation 102, one or more images 34 of the patient are obtained by the medical imaging device 15. In a particular example, the acquired images 34 are X-ray images 34. To acquire the X-ray images 34, the electronic controller 20 is configured to control the medical imaging device 15 (i.e., an X-ray scanner) to acquire the X-ray images 34 of the upper airway or respiratory tract (e.g., from the nose or the mouth to the carina) of the patient P. The X-ray images 34 are acquired over time (i.e., during MV of the patient P) and each X-ray image 34 can have a timestamp 36 corresponding to an acquisition time of the image 34.

At an operation 104, the electronic processing device 18 (or the mechanical ventilator 2) receives the X-ray images 34, and is configured to process the X-ray images 34 to generate timeline images 38 at corresponding discrete time points (i.e., based on the timestamps 36 for each X-ray image 34). The image processing operation 104 can include a variety of examples. In one embodiment, the image processing operation 104 can include aligning the X-ray images 34 to a reference viewpoint. In another embodiment, the image processing operation 104 can include normalization of grayscale values of the X-ray images 34. In another embodiment, the image processing operation 104 can include performing deformable image registration (DIR) of the X-ray images 34. In another embodiment, the image processing operation 104 can include performing a simulated re-projection of the X-ray image 34 from an aligned point and direction of view. In another embodiment, the image processing operation 104 can include interpolating the X-ray images 34 to generate the timeline images 38 at discrete time points separated by a predetermined fixed time interval.

Notably, in some embodiments the image processing operation 104 includes aligning the images to a reference viewpoint. In the common case in which a mobile X-ray or other mobile imaging device 15 is used to image the patient P while the patient P lies on his or her hospital bed, it is difficult to consistently acquire images from the same viewpoint. Typically, the mobile imaging device 15 is rolled into the room of the patient P each day for the imaging acquisition, then moved to other patient rooms for other imaging tasks, and then returned to the room of the patient P the next day for acquiring the chest image of the patient P on that next day. Since the mobile imaging device 15 is thus repositioned for each successive image acquisition (e.g., each day or other time interval between imaging sessions), it is unlikely to be positioned in precisely the same way for each successive image acquisition, resulting in day-to-day differences in the viewpoint of the acquired image. The difficulty in replicating the imaging viewpoint day-to-day when using a mobile imaging device 15 is made even more difficult because the positioning of the imaging device 15 is generally expected to accommodate the bed position of the patient P. While a nurse, imaging technician or other medical professional might attempt some positioning of the patient for the image acquisition, it cannot be expected that the patient will be positioned in precisely the same way from day-to-day, and differences in patient position thus also contribute to differences in imaging viewpoint from day-to-day. Even further, the patient P may be connected with various patient monitoring apparatuses (e.g., vital sign monitors), have pillows or other personal comfort items, or so forth that may change from day to day and can further complicate positioning of the mobile medical imaging device 15.

It might be expected that the DIR can compensate for these types of changes in position of the patient relative to the imaging device 15. However, a 2D-based mere warping-type of DIR only compensates for shifts of the anatomy within the imaging plane, and does not compensate for changes in viewpoint which correspond to a shift of the imaging plane itself.

Hence, to compensate for changes in imaging viewpoint from one imaging session to the next as expected herein, the image processing operation 104 may perform viewpoint correction in which the images 34 are aligned to a reference viewpoint. For example, image transformations used in adjusting for differences in imaging viewpoint during portraiture imaging can be applied to align the images to a reference viewpoint. See Cao et al., "3D aided duet GANs for multi-view face image synthesis", IEEE Trans. on Information Forensics and Security, vol. 14 issue 8 (August 2019); Wang et al., "Head Pose Estimation via Manifold Learning", 2017 DOI: 10.5772/65903. (A change in "pose" is equivalent to a change in "viewpoint", the difference being only in whether one considers the imaging subject or the camera to have moved. As used herein, the "viewpoint" correction suitably corrects for change in position of the imaging device, a change in the patient position, or some combination thereof.) In one suitable approach, viewpoint correction is applied first so that the images are all from the same reference viewpoint, followed by DIR.

Figure 3:
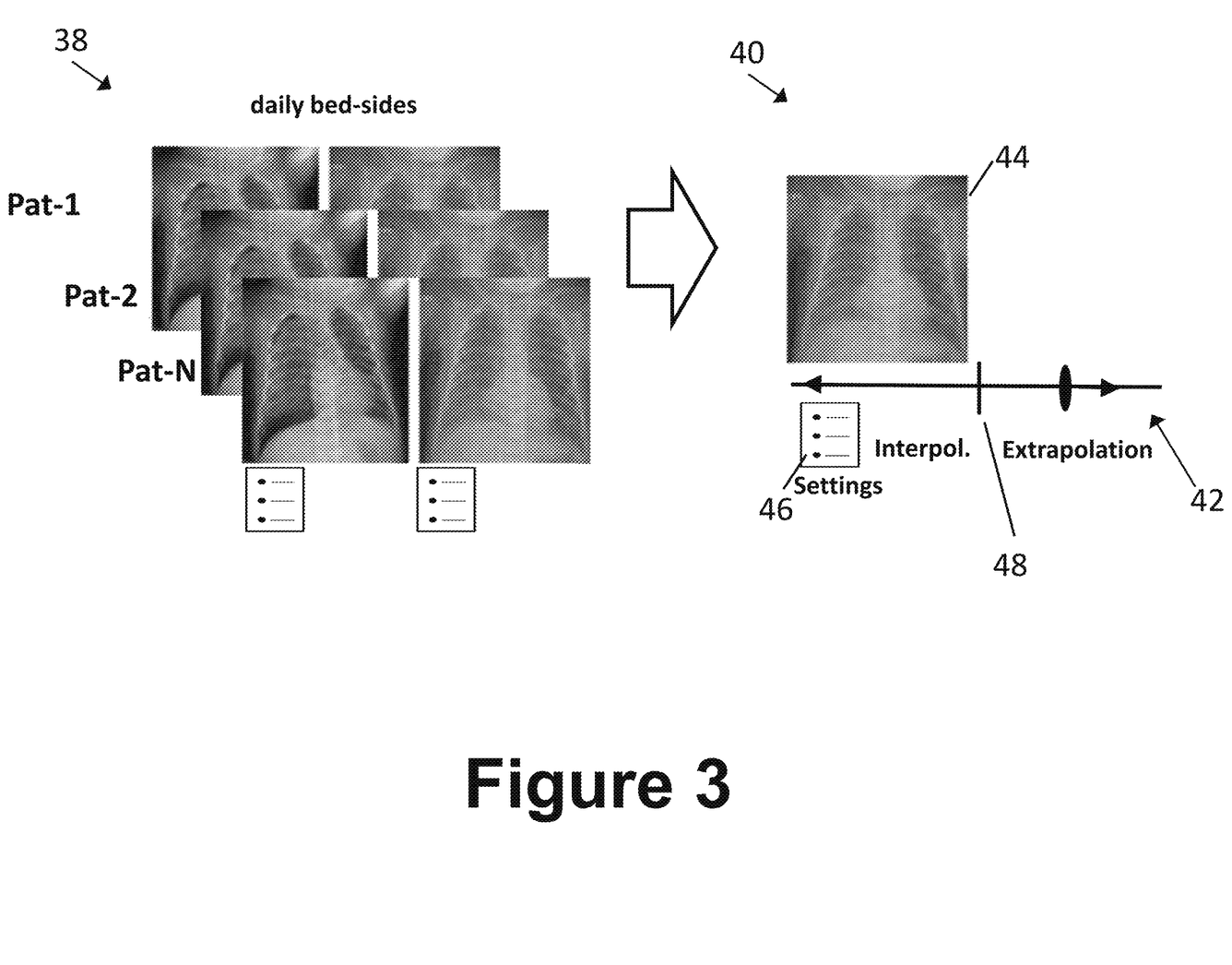
FIGS. 3 and 4 show exemplary timelines generated by the system of FIG. 1.

At an operation 106, a timeline 40 of the timeline images 38 is generated. FIG. 3 shows an example of the generation of the timeline 40. The timeline images 38 are processed to generate the timeline 40. As shown in FIG. 3, the timeline 40 includes a time axis 42 that is scrollable, and a time window 44 in which the timeline images 38 are displayed. The time axis 42 can comprise a slider 42 configured to receive a user input (i.e., a finger tap or finger swipe from a clinician) to dynamically adjust the time window 44 to view different timeline images 38. The timeline 40 also includes a settings field 46. In one example, the settings field 46 can be selected by a user to select a stiffness degree of an image registration between adjacent timeline images 38 in the timeline 40. To do so, the 'stiffness' (or elasticity) of the image registration can be controlled by a desired degree of mutual information (or cross-entropy) between subsequent interpolated timeline images 38. Higher entropy corresponds to less visual flicker, but could ultimately suppress relevant progression features.

In addition, a clinician can select one or more of the timeline images 38 to view additional information (e.g., time, MV settings, and so forth) about the selected timeline image 38. As shown in FIG. 3, the timeline 40 can comprise an interpolation of timeline images 38 (i.e., showing a current and past status of the patient P along with MV settings of the mechanical ventilator 2), allowing the clinician to scroll back and forth to get an overview over the progression, in conjunction with the respective time-dependent MV settings. In addition to the MV settings, recorded blood gas analysis results are added to the settings field 46 (e.g., pH, Ve, Vt, $etCO_2$, etc.). If available, recorded information relative to the cardiovascular system is be added (e.g., HR, BP, ejection fraction, stroke volume, etc.). This allows the clinician to assess a complete picture of the patient status. The timeline images 38 can also be annotated with the values of one or more ventilator setting(s) corresponding in time to the displayed timeline images 38.

As further shown in FIG. 3, the timeline 40 can optionally comprise an extrapolation of timeline images 38 (i.e., showing an estimated future status of the patient P along with MV settings of the mechanical ventilator 2), allowing the clinician to predict progression of the patient P, in conjunction with the respective time-dependent MV settings. To do so, the timeline 40 includes an endpoint 48, and the clinician can select a "future" discrete time point on the timeline 40 that is past the endpoint 48 (i.e., to the "right" of the endpoint 48). An extrapolated timeline image 38 can be generated, and displayed on the timeline 40. In other examples, the non-transitory computer readable medium 26 of the electronic processing device 18 can store treatment data of historical patients, and the extrapolated images 38 can be generated using this treatment data.

Figure 4:
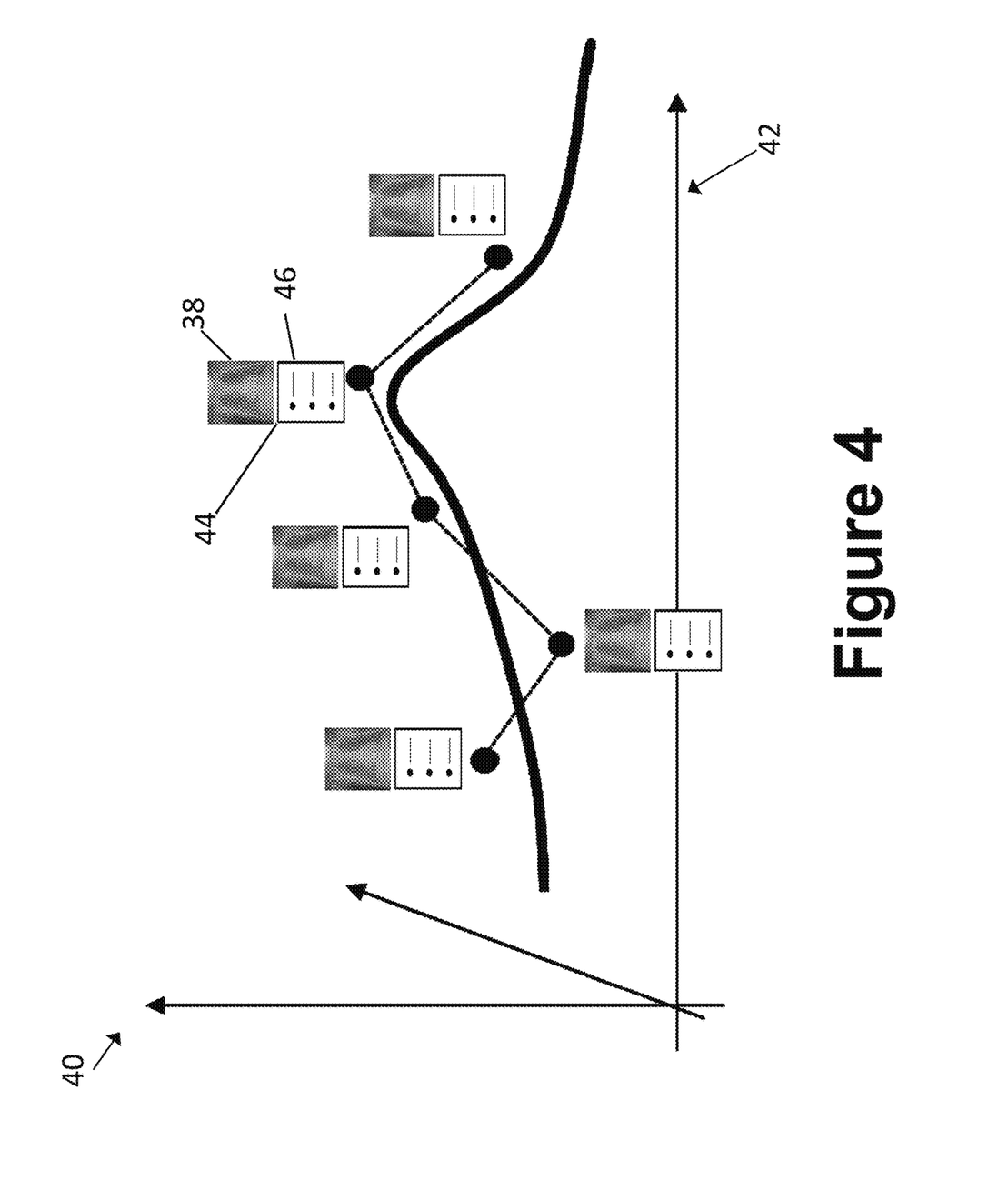

FIG. 4 shows an example of a timeline 40 for display on the display device 14 of the mechanical ventilator 2. The timeline 40 shown in FIG. 4 includes five timeline images 38 in five different time windows 44 at a corresponding number of time points along the time axis 42. In some examples, a clinician can select one of the timeline images 38, and the received X-ray images 34 whose timestamp 36 is closest to the discrete time point of the user-selected timeline image 38 can be displayed. The dashed lines show an un-interpolated version of the images, which can include undesirable flicker. The smoothed line connected the points represents the interpolation.

The interpolation and extrapolation of the X-ray images 34 between sparse time points is achieved in a multi-dimensional imaging space. For example, each two-dimensional (2D) X-ray image 34, with the accompanying MV settings, is denoting one point in this space, forming a progression trajectory. For the interpolation (or "retrospective") process, the multi-dimensional imaging space can include, for example, spatial coordinates (e.g., the X-ray device 15 relative to the patient P, which can include 6 parameters for position and attitude of X-ray source and detector of the X-ray device 15 relative to the patient P), dynamic image intensity parameters (e.g., comprising at least 2 parameters for image intensity distribution ("level" and "window"), respiratory phase dimensions (at least one parameter, which can be controlled by triggering the mechanical ventilator 2), MV settings (such as PEEP and volumes, and includes at least one parameter), and time. Each of the recorded X-ray images 34 is considered as one sample in this, for example, 11-dimensional space. The synthetization of a 'registered' image (i.e., having a same patient-relative view-point, same image intensities, same respiratory phase, and so forth) is computed as an interpolation for a given time point in this space, using an appropriate mathematical interpolation technique. The interpolation allows regularization by a 'stiffness' parameter vector (i.e., inverse 'elasticity').

The computation of a virtual intermediate image is achieved by a mathematical embedding, such as finding a subspace to the overall N-dimensional space, with few degrees of freedom, which is traversed by a trajectory. For a given time point, a projection is performed onto the trajectory, and an image and MV-setting generated for this point.

For extrapolation (i.e., predicting future progression), two options can be used. First, at least one additional interpolation spaced from a "similar" historical patient (as defined by a vector space metric that can be selected). Second, the N-dimensional space of one patient can be extended with dimensions from other patients. Rather than adding one dimension for each other prior patient (e.g., N+K dimensions for K other patients), a (non-linear) dimension reduction technique is employed (e.g., Locally-Linear-Embedding (see, e.g., S. T. Roweis, L. K. Saul, Nonlinear Dimensionality Reduction by Locally Linear Embedding, Science vol 290, 2000; https://en.wikipedia.org/wiki/Nonlinear_dimensionality_reduction), to represent typical patient modes (types) and progression trajectories.

In some embodiments, multivariate, non-linear interpolation between sparse samples can be computed efficiently from a number of mathematical techniques, in particular by manifold learning (see, e.g., Duque et al., "Extendable and invertible manifold learning with geometry regularized autoencoders", arXiv: 2007.07142, 2020), and/or light field rendering for image generation (see, e.g., Koniaris B, Kosek M, Sinclair D, Mitchell K, Real-time Rendering with Compressed Animated Light Fields, Disney Research, Proc. Graphics Interface 2017).

In some embodiments, rather than using interpolation and extrapolation techniques, convolutional neural networks (CNNs) can be used to generate the timeline 40. The CNNs can be trained, for example, by generating virtual samples (2D projection X-ray images) from three-dimensional (3D) CT images from virtual camera positions and attitudes (see, e.g., Yifan Wang, Zichun Zhong, Jing Hua, DeepOrganNet: On-the-Fly Reconstruction and Visualization of 3D/4D Lung Models from Single-View Projections by Deep Deformation Network, arXiv: 1907.09375v1, 2019; J Cao, Y Hu, B Yu, R He, Z Sun: 3D aided duet GANs for multi-view face image synthesis, IEEE Trans. on Information Forensics and Security, 2019). Specifically, the use of an internal four-dimensional (4D) representation of the lung helps to generate the desired mode of visualization. In a setup phase, a 3D model of the lung is set up either from a generic model or from a 3D CT scan of the thorax. Subsequently, the 3D model is adapted to the series of 2D X-ray images, e.g., by using AI (e.g., DeepOrganNet). This generates an internal 4D representation of the lung (i.e., 3D space and time). Only a few discrete time points (namely the time points where the x-rays have been taken) are available. A representation that is continuous in time can be generated by interpolation. To visualize the 4D representation, the 4D model can be used to generate virtual x-ray images in a pre-defined geometry (i.e., anterior-posterior). A benefit using such a model can be to change a projection direction. In this embodiment, the virtual X-ray images are the time-line images; In other embodiments, volume-rendered images of the 3D model at the different points in time are used as time-line images.

In some embodiments, in addition to the discrete settings of the mechanical ventilator 2, the generated (i.e., forced) as well as measured (i.e., free-response) signal curves (e.g., pressure, flow, gas concentrations, etc.) recorded by the mechanical ventilator 2 are displayed on the display device 14 according to the user-selected time point (using retrospective interpolation and prospective extrapolation on the basis of other patients).

In some embodiments, the MV settings and the measured free-response signal-curves (as functions of time) are correlated with each pixel in the interpolated (i.e., registered) time series images 38. Correlations above the noise level are conveyed to the clinician by graphically connecting or highlighting correlating locations in the image domain with the settings-/curves-domain.

In some embodiments, physiological parameters (e.g., lung volume, lung aeration, degrees of pneumonia, atelectasis, effusions, etc.) are estimated from the X-ray images 34 and displayed on the display device 14 for each selected time point, using inter- and extrapolation.

In some embodiments, in addition to the MV settings, medication and therapy records are displayed on the display device 14 for each selected time point, using inter- and extrapolation.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A mechanical ventilation device comprising at least one electronic controller configured to:
receive images of lungs of a patient undergoing mechanical ventilation therapy with a mechanical ventilator, the images being acquired over time and having timestamps;
process the images to generate timeline images at corresponding discrete time points;
display a scrollable timeline of the timeline images in a time window on a display device; and
receive a user input from a user to dynamically adjust the time window; wherein the displayed scrollable timeline further includes a selectable option to receive a user input to select a stiffness degree of an image registration between adjacent images in the timeline.

2. A mechanical ventilation method comprising, with at least one electronic controller:
receiving images of lungs of a patient undergoing mechanical ventilation therapy with a mechanical ventilator, the images being acquired over time and having timestamps;
processing the images to generate timeline images at corresponding discrete time points;
displaying a timeline of the timeline images on a display device, wherein the displayed timeline is a scrollable timeline including the timeline images in a time window;
wherein the timeline further includes a selectable option to receive a user input to select a stiffness degree of an image registration between adjacent images in the timeline.

3. The device of claim 1, wherein the at least one electronic controller is configured to process the images to generate the timeline images by operations including one or more of:
aligning the images to a reference viewpoint;
normalizing grayscale values of the images;
performing deformable image registration (DIR) of the images; and
interpolating the images to generate the timeline images at discrete time points separated by a predetermined fixed time interval.

4. The device of claim 1, wherein the at least one electronic controller is further configured to:
receive a user selection of a timeline image of the displayed timeline via a user input device; and
in response to the user selection, display an image of the received images whose timestamp is closest to the discrete time point of the user-selected timeline image.

5. The device of claim 1, wherein the at least one electronic controller is further configured to:
receive values of at least one ventilator setting of the mechanical ventilation therapy as a function of time; and
annotate the displayed timeline images on the display device with the values of the at least one ventilator setting corresponding in time to the displayed timeline images.

6. The device of claim 1, wherein the timeline includes an endpoint, and the at least one electronic controller is programmed to:
receive a user input of a future discrete time point on the timeline that is past an endpoint of the timeline;
generate an extrapolated image for the future discrete time point; and
display the extrapolated image at the future discrete time point on the displayed timeline.

7. The device of claim 6, further comprising a database storing treatment data of historical patients, wherein the extrapolated image is generated using the treatment data.

8. The device of claim 1, wherein the display of the timeline includes a slider displayed on the display device, the slider configured to receive the user input.

9. The method of claim 2, wherein the processing the images to generate timeline images at corresponding discrete time points includes the at least one electronic controller performing one or more of the following:
aligning the images to a reference viewpoint;
normalizing grayscale values of the images;
performing deformable image registration (DIR) of the images; and
interpolating the images to generate the timeline images at discrete time points separated by a predetermined fixed time interval.

10. The method of claim 2, further comprising the at least one electronic controller:
receiving a user selection of a timeline image of the displayed timeline via a user input device; and
in response to the user selection, displaying an image of the received images whose timestamp is closest to the discrete time point of the user-selected timeline image.

11. The method of claim 2, further comprising the at least one electronic controller:
receiving values of at least one ventilator setting of the mechanical ventilation therapy as a function of time; and
annotating the displayed timeline images on the display device with the values of the at least one ventilator setting corresponding in time to the displayed timeline images.

12. The method of claim 2, wherein the timeline includes an endpoint, and further comprising the at least one electronic controller:
receiving a user input of a future discrete time point on the timeline that is past an endpoint of the timeline;
generating an extrapolated image for the future discrete time point; and
displaying the extrapolated image at the future discrete time point on the displayed timeline.

13. The method of claim 12, wherein the extrapolated image is generated using treatment data of historical patients.

14. The method of claim 2, wherein the displaying of the timeline includes displaying a slider on the display device to receive the user input.

* * * * *